United States Patent [19]

Meserol et al.

[11] Patent Number: 4,683,120
[45] Date of Patent: Jul. 28, 1987

[54] BIOLOGICAL FLUID ASSAY SYSTEM

[75] Inventors: Peter M. Meserol; Jesse L. Acker, both of Whippany, N.J.

[73] Assignee: Gamma Biologicals, Inc., Houston, Tex.

[21] Appl. No.: 660,721

[22] Filed: Oct. 18, 1984

Related U.S. Application Data

[63] Continuation-in-part of Ser. No. 546,345, Oct. 28, 1983, abandoned.

[51] Int. Cl.$^4$ .................... G01N 21/07; G01N 35/06
[52] U.S. Cl. .................................. 422/72; 356/246; 356/427; 422/100; 422/102; 422/104; 494/21
[58] Field of Search ............... 356/427, 246; 250/577; 494/21; 422/63-67, 72, 73, 102, 104, 100

[56] References Cited

U.S. PATENT DOCUMENTS

| | | | |
|---|---|---|---|
| 3,532,470 | 10/1970 | Rochte | 422/61 |
| 3,620,678 | 11/1971 | Guigan | 422/66 |
| 3,679,129 | 7/1972 | Livshitz et al. | 422/72 |
| 3,713,775 | 1/1973 | Schmitz | 422/72 |
| 4,148,607 | 4/1979 | Bernoco et al. | 422/72 |
| 4,309,384 | 1/1982 | Trod | 422/72 |
| 4,344,768 | 8/1982 | Parker | 422/72 |
| 4,528,159 | 7/1985 | Liston | 422/63 |
| 4,558,947 | 12/1985 | Wardlaw | 356/40 |

Primary Examiner—Michael S. Marcus
Attorney, Agent, or Firm—Arnold, White & Durkee

[57] ABSTRACT

A biological fluid assay system and method for the determination of immunoreactive characteristics of biological specimen and more particularly for the qualitative determination of immunological reactions. The apparatus includes a centrifuge rotor, a disposable belt mountable on the centrifuge rotor, and a plurality of light transmissive chambers as components of the removable belt, each of the chambers having a vertical apex and a horizontal radial apex for accepting a sample comprising a specimen and an appropriate reagent. An illumination system projects an image of the sample while a linear photosensitive array detects the image of the sample for measuring the vertical dimension of the sample and a microprocessor analyzes the vertical dimension of the sample. A sample is radially accelerated to compress the particulate portion of the sample or reagent into a compact mass in the extreme radial portion of the transparent chamber. The centrifugal force on the sample is balanced with the gravitational force acting on the compact mass by decelerating the rotor. The vertical dimension of the compact mass is measured while the sample is rotating. The vertical dimension of the compact mass is again measured after a delay to determine the presence of vertical streaming. The difference between the vertical dimension of the compact mass before streaming and the vertical dimension of the mass after streaming is completed, due to gravitational attraction, is determined.

15 Claims, 24 Drawing Figures

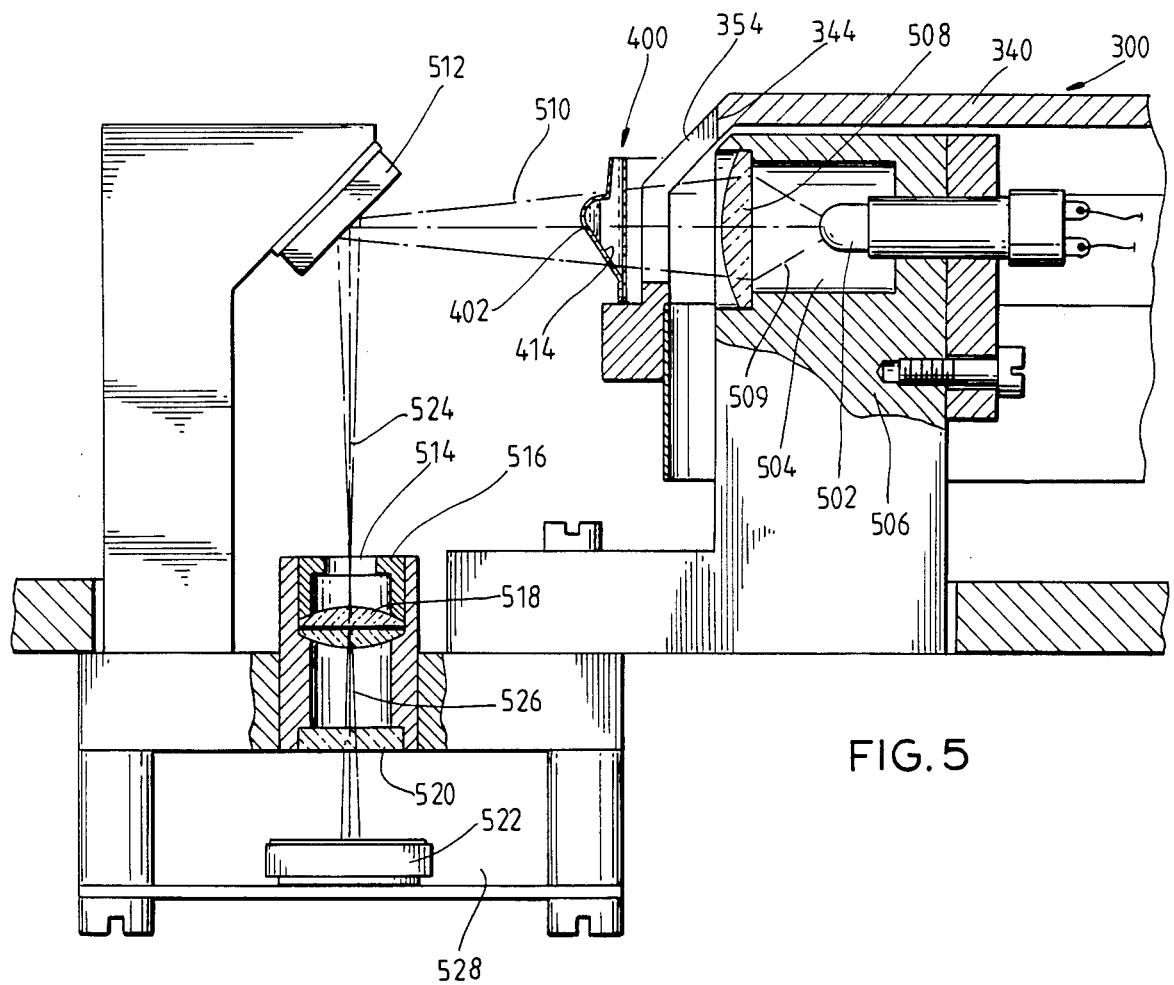
FIG. 5
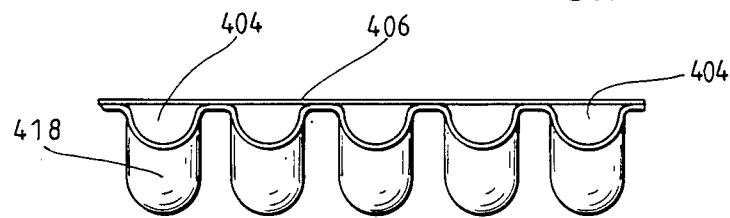
FIG. 7
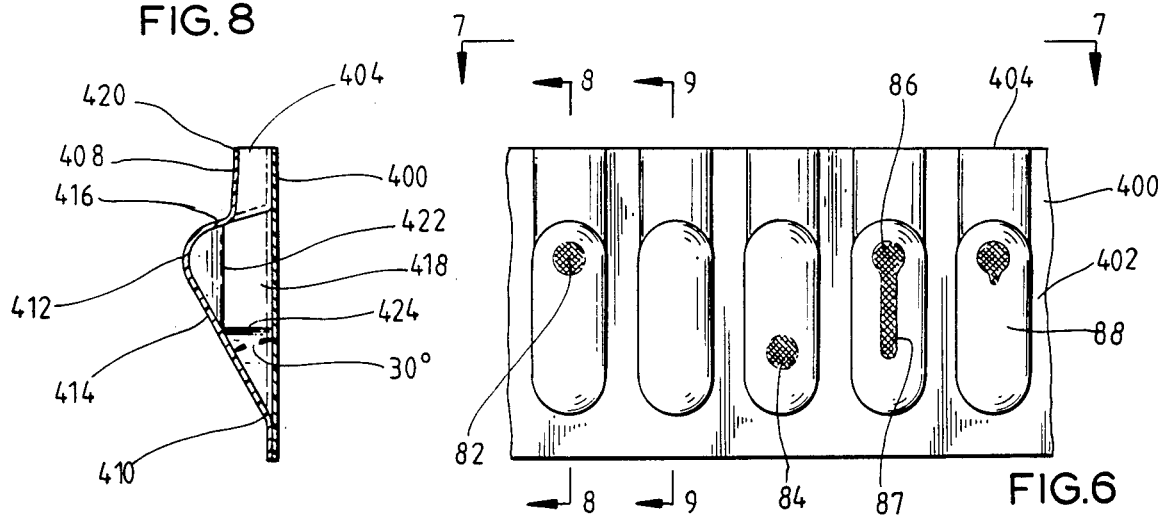
FIG. 8
FIG. 6

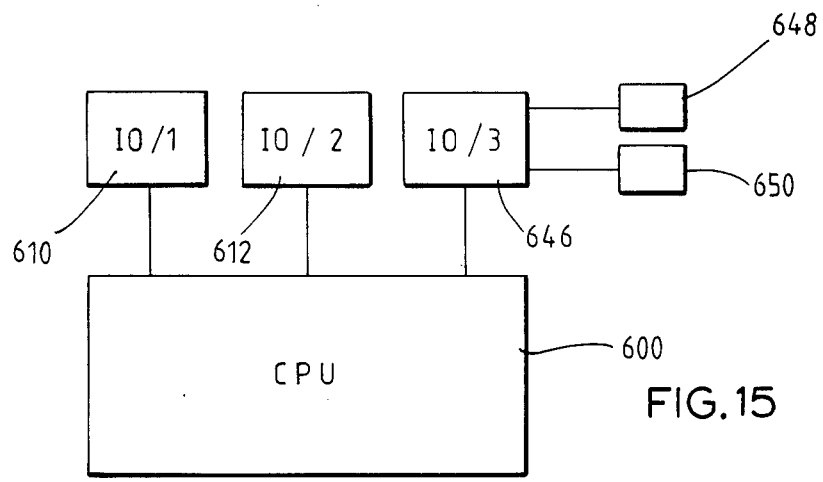
FIG.15
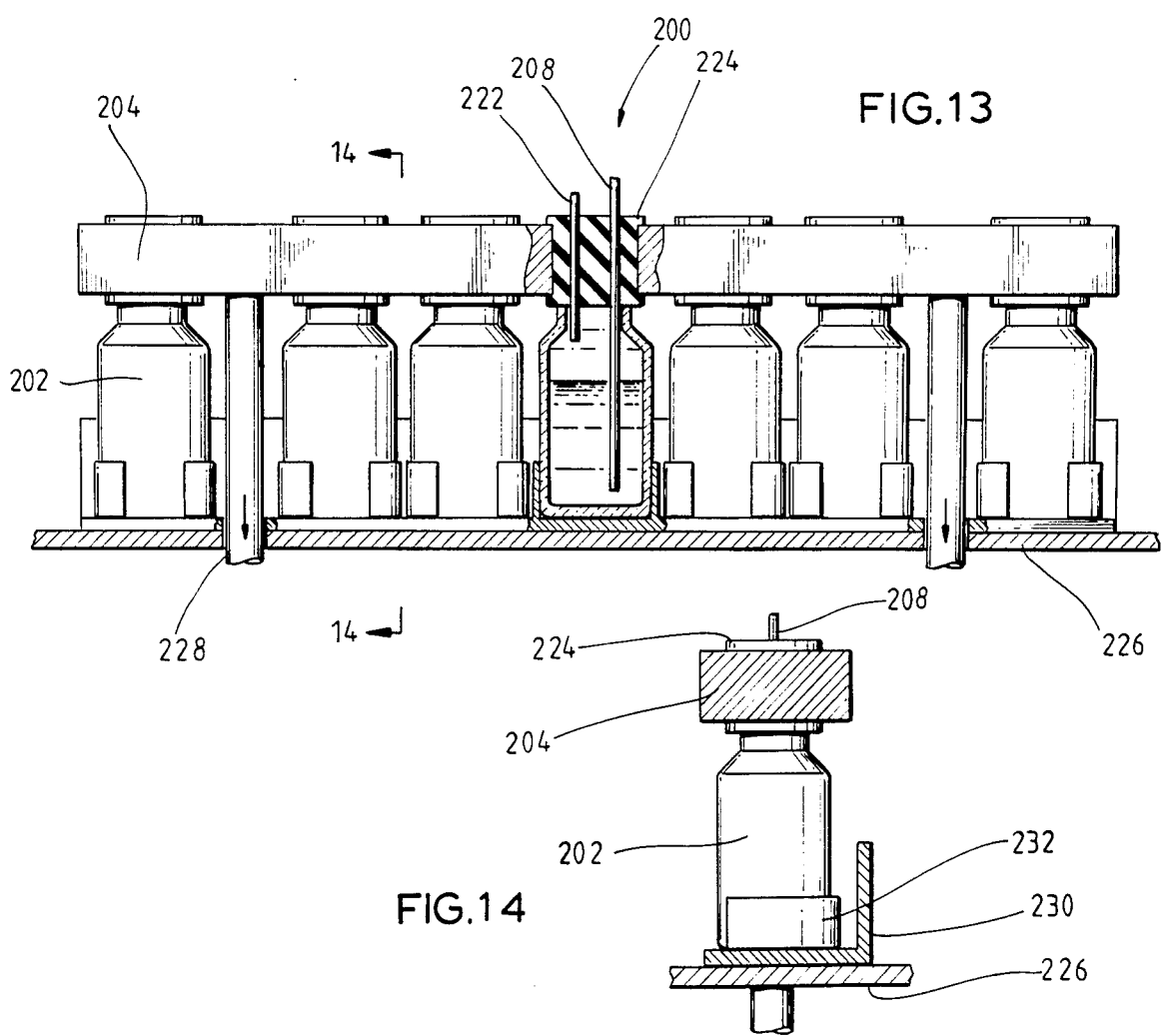
FIG.13
FIG.14

BIOLOGICAL FLUID ASSAY SYSTEM

CROSS REFERENCE TO RELATED APPLICATION

This is a continuation-in-part of prior application Ser. No. 546,345, filed Oct. 28, 1983.

FIELD OF THE INVENTION

The present invention relates to the determination of the reactive characteristics of fluid specimens and more particularly relates to a method and automated apparatus for the qualitative determination of immunological reactions of biological specimens.

BACKGROUND OF THE INVENTION

The microscope slide technique for manually performing blood grouping tests is not sensitive to subtle reactions and requires strict attention to protocol to avoid the possibility of sample misidentification. As an alternative to the microscope slide technique the test tube centrifuge technique has been utilized. Additionally, the test tube centrifuge technique has been used to augment or to confirm the microscope slide technique procedures. The test tube centrifuge technique has the characteristic of being more sensitive to subtle reactions than the microscope slide technique. However, the test tube centrifuge technique is more labor intensive, is subject to interpretation by the laboratory technician and has the inherent problem of assuring accurate sample identification.

The "microwell" test method has been developed to acquire the maximum utilization of the materials involved in blood grouping and to standardize the interpretation and the evaluation of biological specimens to provide more consistent results. The "microwell" test method uses a plate containing numerous small centrifuge tubes or wells.

Automated reading techniques for blood grouping have typically been limited to the measurement of turbidity. Turbidity results from the breakup of centrifuged red blood cells. A method of initiating the dissociation of red blood cells is to mix the cells with a reagent and to subject the mixture to vibration. The dissociation of the red cells is indicative of a negative reaction between red blood cells and the added reagent. If a positive reaction occurs after being subjected to vibration, the red cells remain tightly associated. The cohesive attraction of the red cells when subjected to the reagent is an indication of a positive reaction. Typically, a positive reaction between the red blood cells and the reagent yields a compact mass of red blood cells and a clear supernatant.

Turbidity may be measured based upon the opacity of the specimen. A light or energy beam is transmitted through the specimen. A detector determines the reduction in the intensity of the light or energy beam caused by the scattering or the absorption of the beam by the specimen. The turbidity of the specimen is measured as a function of the reduction in transmitted light or energy. Specifically, the reduction of the intensity of the transmitted beam is caused by the loss of light or energy due to the scattering and the absorption of the incident beam by the suspended red cells. The number of available suspended red cells is directly proportional to the amount of dissociation of red cells caused by negative reactions.

Despite important advances in the prior art, there is still a need for an automated blood grouping system and a method which reduces the subjective interpretation of reactions by laboratory personnel, which is easily used, which requires little technical expertise and few personnel, and which is comparatively inexpensive.

SUMMARY OF INVENTION

Recognizing the need for an improved system and method for automatically determining blood groups, it is, therefore, a general attribute of the present invention to provide a novel automated blood grouping system and method.

A feature of the present invention is to provide a novel automated blood grouping method and system which positively identifies the specimen from each patient.

Another feature of the present invention is to provide a novel apparatus which performs laboratory procedures, normally accomplished manually, in an automatic, completely reproducible sequence, assuring consistent results.

Yet another feature of the present invention is to provide a novel automated blood grouping method which may be performed in rapid succession with an extremely high degree of accuracy.

Still another feature of the present invention is to provide a novel automated blood grouping method and system that accurately determines the biological parameters of blood specimen based upon an accurate evaluation of the reaction, or lack thereof, between a biological specimen and a reagent.

Additional features and advantages of the invention will be set forth in part in the description which follows and in part will become apparent from the description, or may be learned by practice of the invention. The features and advantages of the invention may be realized and obtained by means of instrumentalities, combinations and steps particularly pointed out in the appended claims.

In accordance with one embodiment of the present invention a method for determining the reactive characteristics of a biological fluid specimen begins with the step of preparing a sample including the specimen and an appropriate reagent such that the sample is at least partially opaque. The sample is centrifuged and then a first measurement is made of a linear dimension of an opaque portion of the sample. Thereafter, a subsequent measurement of the same linear dimension of the sample is made. Then the first measured dimension is compared to the second measured dimension.

In accordance with another embodiment of the present invention an apparatus for determining the reactive characteristics of a biological fluid specimen includes a centrifuge rotor and an energy transmissive, flexible belt formable into a cylinder and removably mountable for movement in unison with the rotor. The belt includes means for accepting a plurality of specimens. A detection system irradiates the plurality of specimens contained within said belt and optically measures the reactive characteristics of the specimens.

In further summary, it should be understood that blood grouping according to the present invention is accordingly, relates broadly to a method and an apparatus for differentiating between positive and negative immunological reactions indicated by the affinity of particles associated with a biological specimen and an associated reagent of interest. The present invention also has application in other immunoassays, such as determinations of hepatitis, rheumatoid arthritis, and infectious mononucleosis, where opaque particles other than human red blood cells are used as carriers for immunological agents (antigens). Suitable opaque particles include barium sulphate, latex, animal red blood cells, or any particle to which an antigen of interest may be attached and viewed.

BRIEF DESCRIPTION OF THE DRAWING

The accompanying drawings, which are incorporated in and constitute a part of the specification, illustrate a preferred embodiment of the invention and, together with the general description of the invention given above and the detailed description of the preferred embodiment given below, serve to explain the principles of the invention.

FIG. 5 is a cross-sectional view of the present invention taken generally along section line 5—5 of FIG. 4;

FIG. 6 is an enlarged elevational view of a segment of a disposable belt shown in FIG. 4;

FIG. 7 is a plan view taken along the line 7—7 of FIG. 6;

FIG. 8 is a vertical, cross-sectional view taken generally along the line 8—8 of FIG. 6;

FIG. 13 is an enlarged, cross-sectional, cut-away view illustrating the reagent reservoirs of the reagent dispensing device taken along the section line 13—13 in FIG. 2;

FIG. 14 is a partial cross-sectional view illustrating a reagent reservoir of the present invention taken along the section line 14—14 in FIG. 13;

FIG. 15 is a schematic diagram illustrating the microprocessor system of the present invention;

DESCRIPTION OF THE PREFERRED EMBODIMENT

Figure 1:
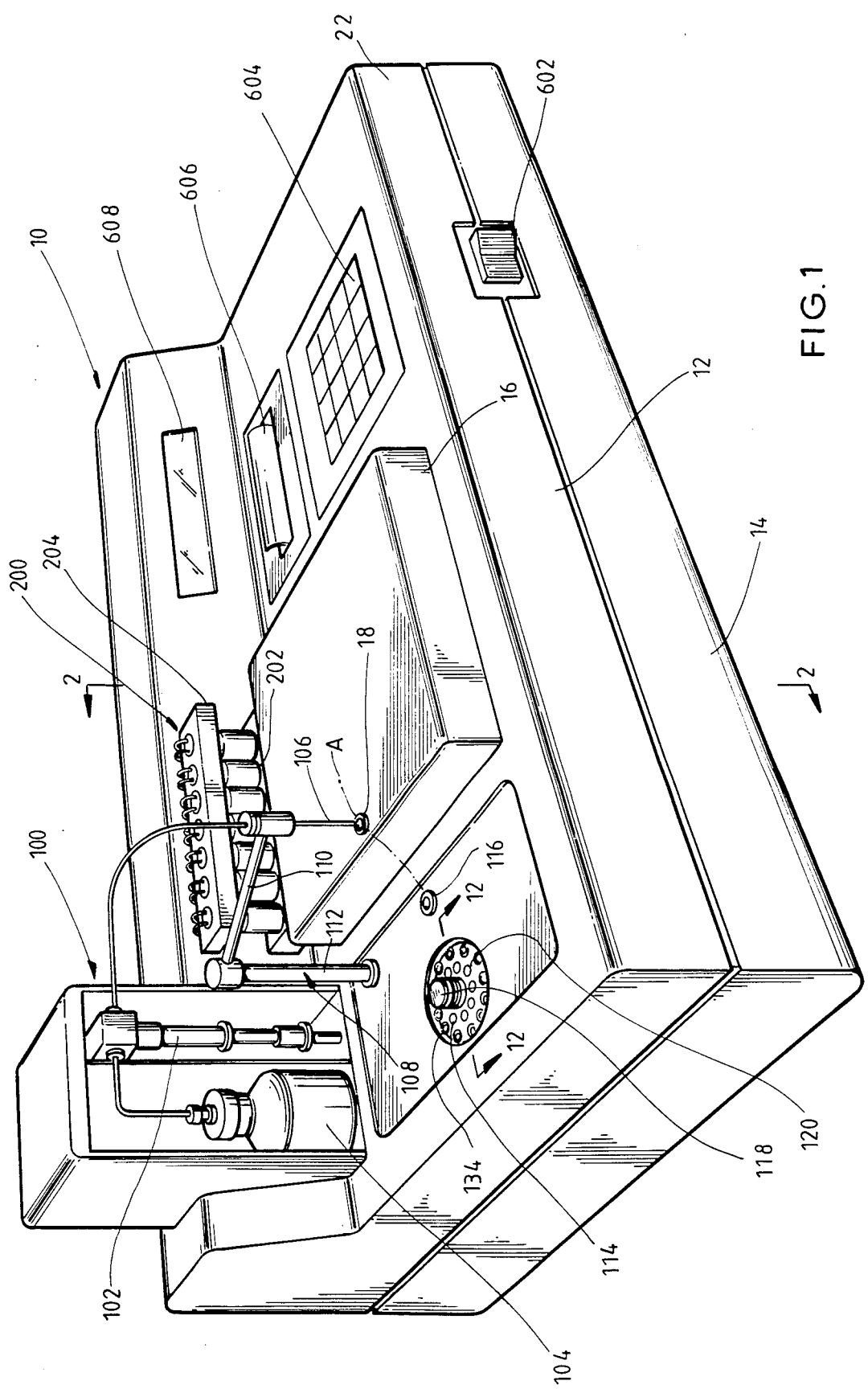
FIG. 1 is a perspective view of one embodiment of the automated blood grouping system of the present invention.
Figure 2:
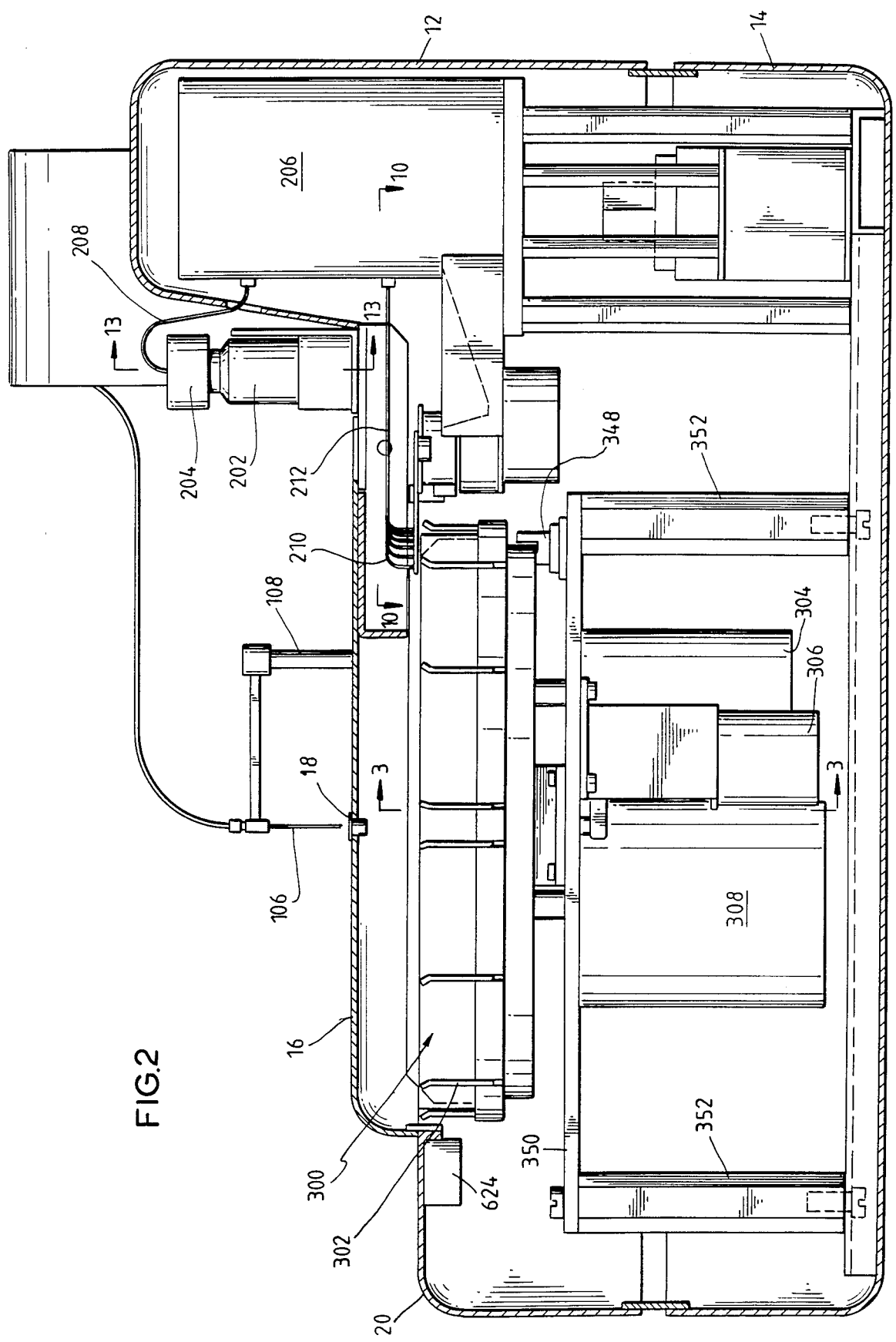
FIG. 2 is a cross-sectional view taken generally along section line 2—2 in FIG. 1

Referring to the drawing wherein like reference characters are used for like parts throughout the several views, a biological fluid assay apparatus 10, shown in FIGS. 1 and 2, includes a centrifuge rotor 300, a single use belt 400 mounted on the rotor 300, a microprocessor 600, an optical system 500, a pipetter-diluter device 100 and a reagent dispensing device 200. The biological fluid assay apparatus 10 also includes a housing 11 having a top structure 12 with a planar work surface 20, on which various controls are located, and a bottom structure 14. The biological fluid assay apparatus 10 is electrically activated by a switch 602 on the front vertical side 22 of the top structure 12. The operator utilizes a keyboard 604 to input the appropriate test information and access the desired test results. The resultant analysis can be printed on a printer 606 or displayed on a display 608.

The removable carousel 114 of the pipetter-diluter device 100 accepts test tubes 134 in an upright configuration. The tubes 134, accepted along the periphery of the carousel 114 in openings 124 conforming to the cross-sections of the tubes 134, have been previously centrifuged in a conventional centrifuge device to separate, by density, specimens of interest contained therein. An empty dilution cup 134a corresponding to each tube 134 is accepted in the inner ring of openings 122 conforming to the cross-sections of the cups 134a. The dilution cups 134a are used to contain liquid for diluting the specimen removed from the specimen tubes 134. The cups 134a may be conventional Krone cups with V-bottoms 122.

Figure 12:
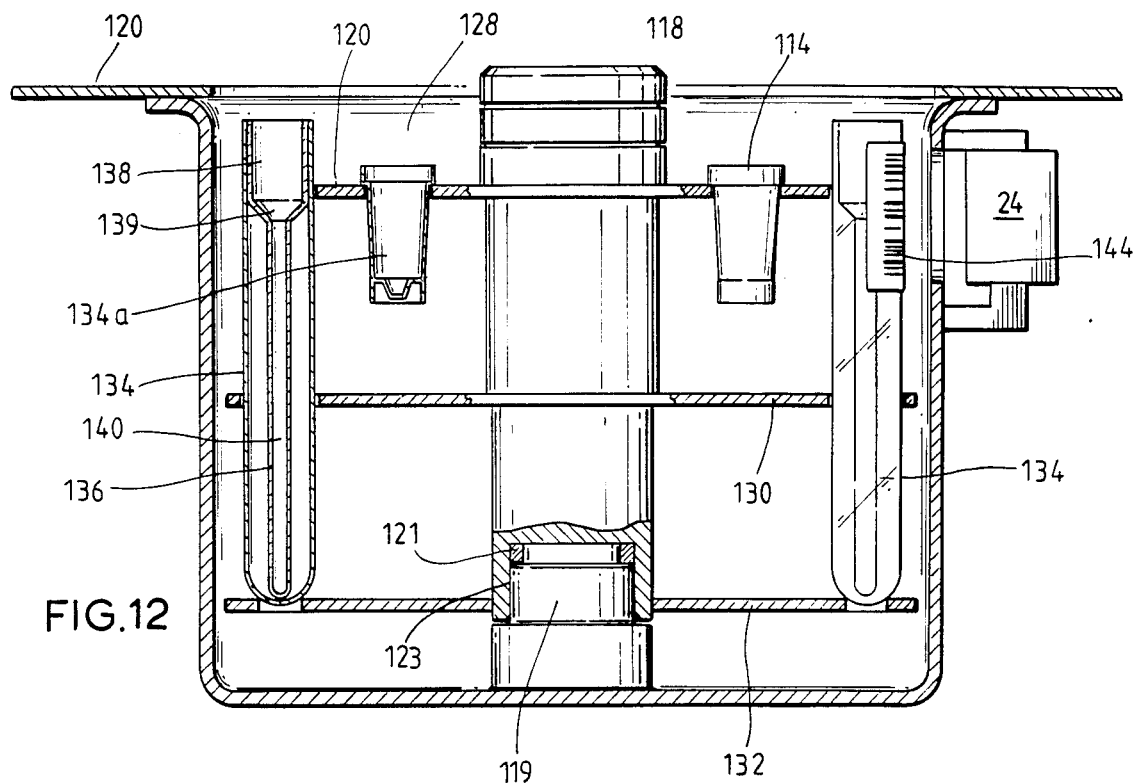
FIG. 12 is a cross-sectional view taken generally along the section line 12—12 in FIG. 11.

As illustrated in FIG. 12, the carousel 114 includes a stanchion 118 that supports the top plate 120, the middle plate 130 and the bottom plate 132. The cups 134a are supported by their lips 124 on the top plate 120. The test tubes 134 are supported atop the bottom plate 132 by the middle plate 130 and top plate 132.

The carousel 114 is removably held in the trough 128 below the planar work surface 20 of the biological fluid assay apparatus 10. The center stanchion 118 of the carousel 114 extends slightly above the planar work surface 20. On its lower end, the stanchion 118 telescopes over an axle 119 with radially outwardly directed tabs 121 that engage slots 123 in the inside surface of the stanchion 118.

The test tubes 134 may be adapted to hold a smaller volume, while having sufficient height to permit definition of the layers within a specimen, through the use of the removable inserts 136. Each insert 136 includes an upper enlarged diameter funnel portion 138 that frictionally mates with the inside wall of a test tube 134. A narrow channel 140 extends downwardly through the test tube 134 from the conical bottom 139 of the portion 138. In this way a conventional test tube 134, having a volume of 6 to 7 milliliters for example, is adapted to contain a lesser volume, for example about 1 milliliter, in the insert 136, which has substantially the same height as the test tube 134.

A coded bar label 144 fits on the exterior facing side of the tubes 134. Therefore, the optical bar code reader 24 may positively identify all specimens through their labels 114. The carousel 114 may be atomatically rotatively indexed to align successive tubes 114 with the reader 24 or to orient a tube 134 in a desired position, through the rotation of the stanchion 118 by the axle 119.

The support plate 350, in turn supported by the stanchions 352. The pivotal cover 16 encloses the centrifuge rotor 300 inside the biological fluid assay apparatus 10. The cover 16 can be lifted to provide access to the centrifuge rotor 300.

The pipetter-diluter device 100 includes a syringe 102 and a conduit needle 106 in fluid communication. The needle 106 is automatically moved from location to location by the L-shaped rotating and reciprocating arm 108. The arm 108 comprises the vertical stanchion 112 and the horizontal stanchion 110.

To prevent contamination caused by utilizing the conduit needle 106 and the syringe 102 with different fluids, a needle wash station 116 is used to wash the conduit needle 106 and the syringe 102 between contact with the different fluids. The wash station 116 is located along the arc "A", shown in FIG. 1, circumscribed by the needle 106 as it pivots with the arm 108 to and from the appropriately aligned tubes 134 and cups 134a.

The reagent reservoirs 202 are located on top of the planar work surface 20 and are secured by the reservoir cover 204. The reagent reservoirs 202 are connected to the reagent pump 206 by the exit tubes 208. The reagent pump 206 is enclosed in the upwardly protruding section of the top structure 12 that lies above the planar work surface 20. The reagent pump 206 provides reagent to the outlets 210 by the tubes 212.

Figure 3:
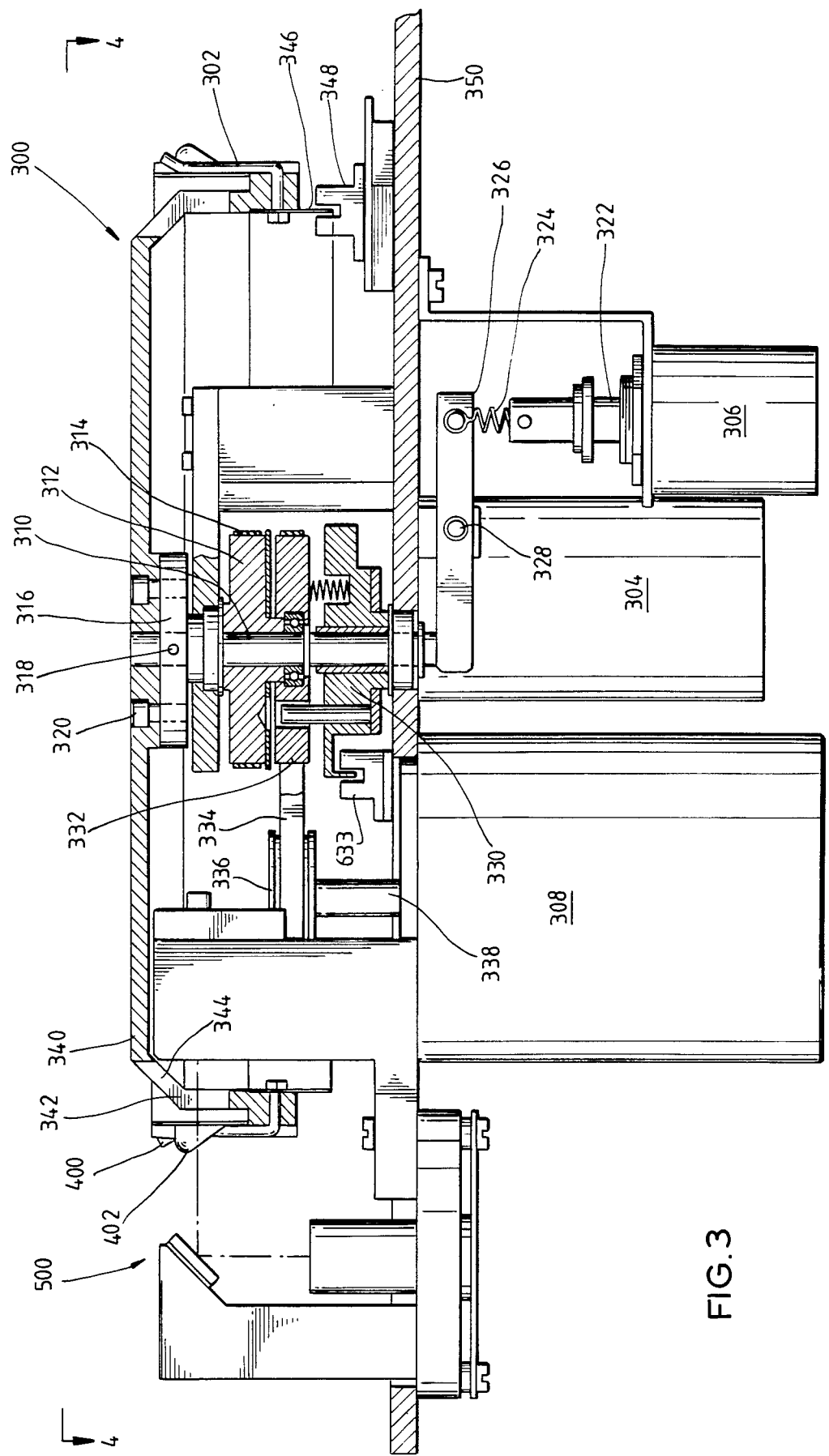
FIG. 3 is a cross-sectional view taken along section line 3—3 in FIG. 2

The electrical components associated with the centrifuge rotor 300 are located below the support plate 350, as shown in FIGS. 2 and 3. The variable speed motor 304, the stepping motor 308 and the solenoid 306 are located blow the support plate 350. The variable speed motor 304 is connected to the centrifuge rotor 300 by a series of shafts and pulleys. The stepping motor 308 is engaged and disengaged by the solenoid 306, as shown in FIG. 3. The solenoid 306 draws the movable core 322 into an inner coil (not shown) when current flows through the solenoid 306. As the movable core 322 is pulled through the spring 304 into the solenoid 306, the lever 326 is pivoted about the pivot point 328. When the lever 326 pivots about the pivot point 328, the clutch 330 is forced to engage the pulleys 312 and 332. The pulley 312 is driven by the variable speed motor 304 utilizing the belt 314. The pulley 332 is driven by the belt 334 which is operationally associated with the stepping motor 308. The stepping motor 308 is connected to the pulley 332 by the shaft 338 and the pulley 336. The main shaft 310 is fixed to the centrifuge rotor 300 by the mounting plate 316.

Figure 4:
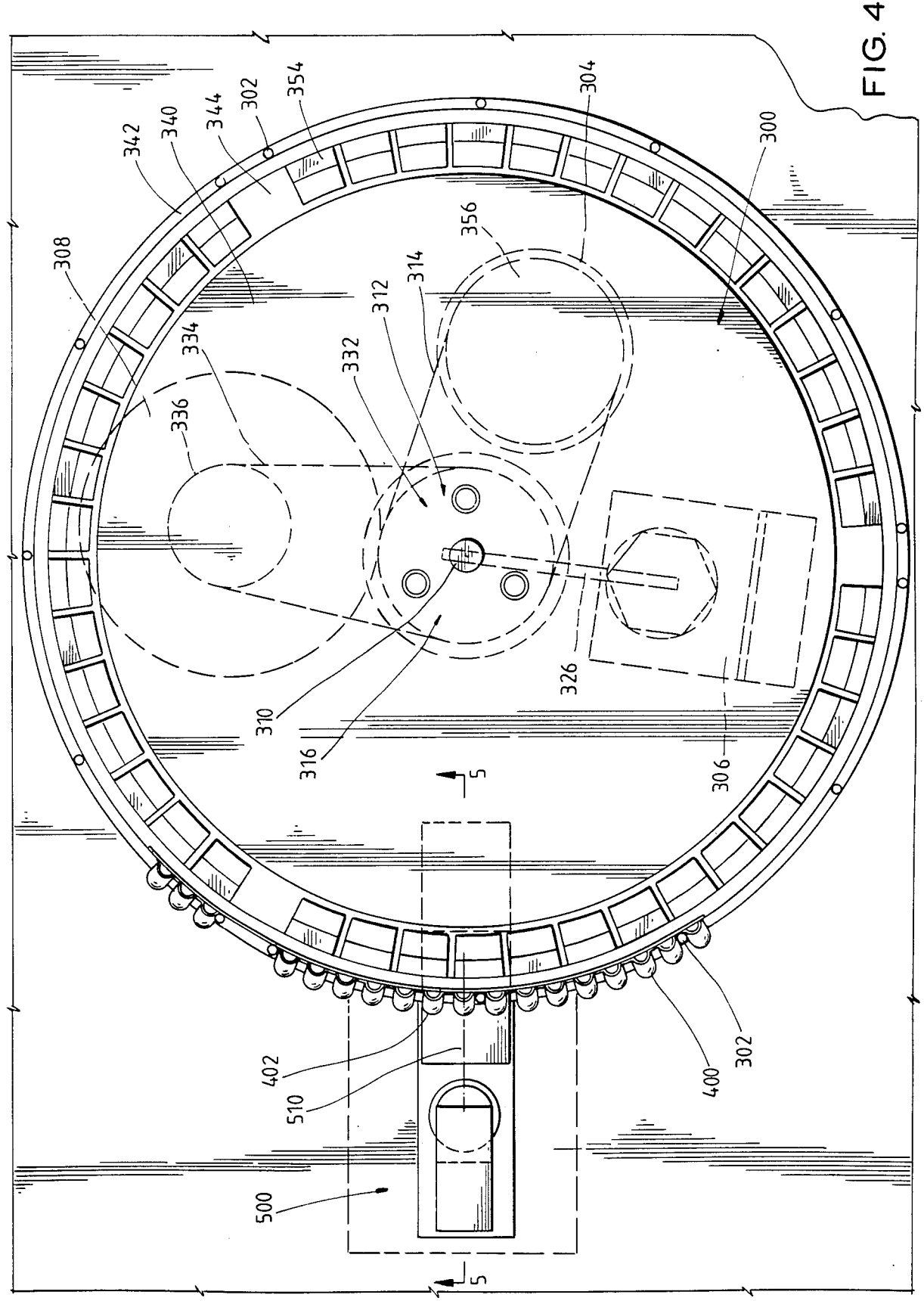
FIG. 4 is an enlarged plan view taken generally along section line 4—4 in FIG. 3.

As shown in FIG. 4, the variable speed motor 304 drives the pulley 356, the belt 314, the pulley 312, the shaft 310, the mounting plate 316 and ultimately the centrifuge rotor 300. The stepping motor 308 drives the stepping motor pulley 336, the belt 334, the pulley 332, the shaft 310, the mounting plate 316 and ultimately the centrifuge rotor 300.

The single use belt 400 encircles the centrifuge rotor 300 as shown in FIG. 3. The single use belt 400 is held in place by the belt supports 302 located between the cuvettes 402 of the single use belt 400 which may be a strip folded upon itself to assume a cylindrical configuration. Generally, the single use belt 400 can be made of any material that is translucent, transparent or pellucid to light. The belt 400 can be made of transparent, flexible plastic such as PVC, styrene, cellulose acetate, cellulose butyrate, or any relatively inert, light transmissive, wettable plastic material that is compatible with biological reagents used in the testing of biological specimens. Additionally, it is preferred that the belt 400 be made of a suitable translucent material that diffuses the light and provides a more uniform illumination of the sample to enhance the optical resolution.

As shown in FIGS. 6, 7 and 8 each cuvette 402 in the belt 400 is formed from an elongate flat strip 406 fixed to the elongate, indented strip 408 shaped by vacuum forming or the like. The flat strip 406 and the indented strip 408 form the inlets 404 and the chamber 418. One embodiment of the present invention utilizes a single use belt 400 having eighty-four cuvettes 402, for example, with seven cuvettes 402 available for each series of reactions required to determine the blood group of a patient. Thus, twelve patient specimens can be analyzed using a single use belt 400 having eighty-four cuvettes 402.

The vertically aligned, convex chambers 418 smoothly extend radially outwardly. Each cuvette 402 is formed in the shape of an angled, inverted test tube portion extending upwardly and outwardly from the vertical plane defined by the strip 406. Each cuvette 402 is broadly semi-elliptical in shape when viewed from above, as shown in FIG. 7. Typically, the indented strip 408 is heat sealed to the flat strip 406. As shown in FIG. 8, a vertical apex 410 is located at the bottom of the chamber 418. The moderately inclined segment 414 increases in depth, to a radial apex 412. The segment 414 may be oriented at an angle of about 30° with respect to the strip 406. The spherically shaped radial apex 412, having the shape of the bottom of a conventional test tube, is the most outwardly radially extending part of the cuvette 402. After the radial apex 412, the outline of the cuvette 402 is angled sharply back toward the strip 406 by the segment 416. Each cuvette 402 then extends vertically upwardly along a uniformly shallow generally vertical segment 420. The uniformly shallow generally vertical segment 420 in conjunction with the flat strip 406 form the inlet 404.

The smooth characteristics of the cuvette 402 greatly enhance the utilization of the present invention. The smoothly curved surfaces associated with the indented strip 408 provide very little physical resistance to the movement of fluid thereupon for enhancing the sensitivity of the biological fluid assay system 10. Thus, surface tension is minimized, flow characteristics are enhanced and a better qualitative determination of the characteristics of the immunological reaction is possible.

The centrifuge rotor 300 is comprised of a top plate 340, an annular plate 344 and a cylindrical member 342, as shown in FIG. 3. The top plate 340 is fixed at right angles to the central axis of the cylindrical member 342. The top plate 340 and the cylindrical member 342 are secured to the annular plate 344. The annular plate 344 and the cylindrical member 342 have a plurality of aligned apertures 354. The apertures 354 are approximately the width of two of the cuvettes 402 on the belt 400. Typically, as illustrated in FIG. 4, two of the cuvettes 402 are aligned directly in front of each aperture 354 when the single use belt 400 is engaged with the centrifuge rotor 300. The orientation of the single use belt 400 is maintained by the belt supports 402. The belt supports 402 abut one or more cuvettes to positionally secure the single use belt 400 on the centrifuge rotor 300. Thus, as illustrated in FIG. 3, when the centrifuge rotor 300 revolves, each individual cuvette 402 on the single use belt 400 passes through the optical system 500 for analysis. The centrifuge rotor 300 is steadily guided by the rotor guide 346 and mating slotted member 348.

The conduit needle 106 and syringe 102 withdraw specimen from each specimen tube 134 for deposit either in a cuvette 402 (See FIGS. 3-8) or in a dilution cup 134a. After specimen has been introduced, the conduit needle 106 and the syringe 102 are used to deposit diluent into the dilution cups 134a. The specimen/diluent solution is withdrawn from the dilution cups 134a by the conduit needle 106 and the syringe 102 for deposit in a cuvette 402. The conduit needle 106 acquires access to the cuvettes 402 in the single use belt 400 by passing through the aperture 18 in the cover 16. The diluent is maintained in the diluent reservoir 104. The syringe 102 extracts the diluent from the reservoir 104 and passes the diluent through the conduit needle 106 to the dilution cups 134a.

The appropriate angular acceleration of each cuvette 402 by the centrifuge rotor 300 is important. The centrifugal force causes the red cells to form a small round compact mass 92 as shown in FIGS. 9B-9E. With sufficient centrifugal force, the compact mass 92 forms at the radial apex 412 of the cuvette 402. In the illustrated embodiment, the centrifuge rotor 300 accelerates to a velocity sufficient to impart a centrifugal force to the red cells in the specimen at a magnitude of about 600 G's which corresponds to approximately 2100 revolutions per minute. The centrifuge rotor 300 maintains this speed for approximately 35 seconds.

When the compact mass 92 is sufficiently concentrated and compacted by the centrifugal force, the motor 304 is automatically deenergized. Without the aid of the motor 304, the centrifuge rotor 300 decelerates. When the centrifuge rotor 300 reaches a speed at which the force of gravity automatically equals the centrifugal force along the inclined segment 414 due to the rotation of the centrifuge rotor 300, the stepping motor 308 engages the shaft 310 of the centrifuge rotor 300 by utilizing the belt 334. The stepping motor 308 provides the force to drive the centrifuge rotor 300 at a speed that approximately balances the gravitational and centrifugal components of the force along the inclined segment 414 of the cuvette 402. Typically, the stepping motor 308 drives the centrifuge rotor 300 at approximately 60 revolutions per minute or slightly less than 1G.

The optical system 500 includes the light source 502 affixed in the stationary member 506 and extending into the optical chamber 504 of the member 506, as shown in FIG. 5. The rays 509 of light emitted by the light source 502 impinge upon the lens 508. The lens 508 focuses the rays 510 through the aperture 354 in the centrifuge rotor 300 and through the cuvette 402. Further, the lens 508 causes the rays 510 to converge toward the reflector 512. The rays 510 impinge upon the reflector 512 and are redirected as rays 524. The rays 524 pass into the lens box 516 through the slit 514. Once inside the lens box 516, the rays 524 pass through the lens 518. The lens 518 focuses the rays 526 through the transmissive surface 520 onto the linear optical detector 522. The linear optical detector 522 is enclosed in the chamber 528 to prevent extraneous readings due to outside light sources. Since the light source 502 is oriented perpendicularly to a vertical plane, only the vertical dimension of the specimen in each cuvette 402 is imaged.

Figure 10:
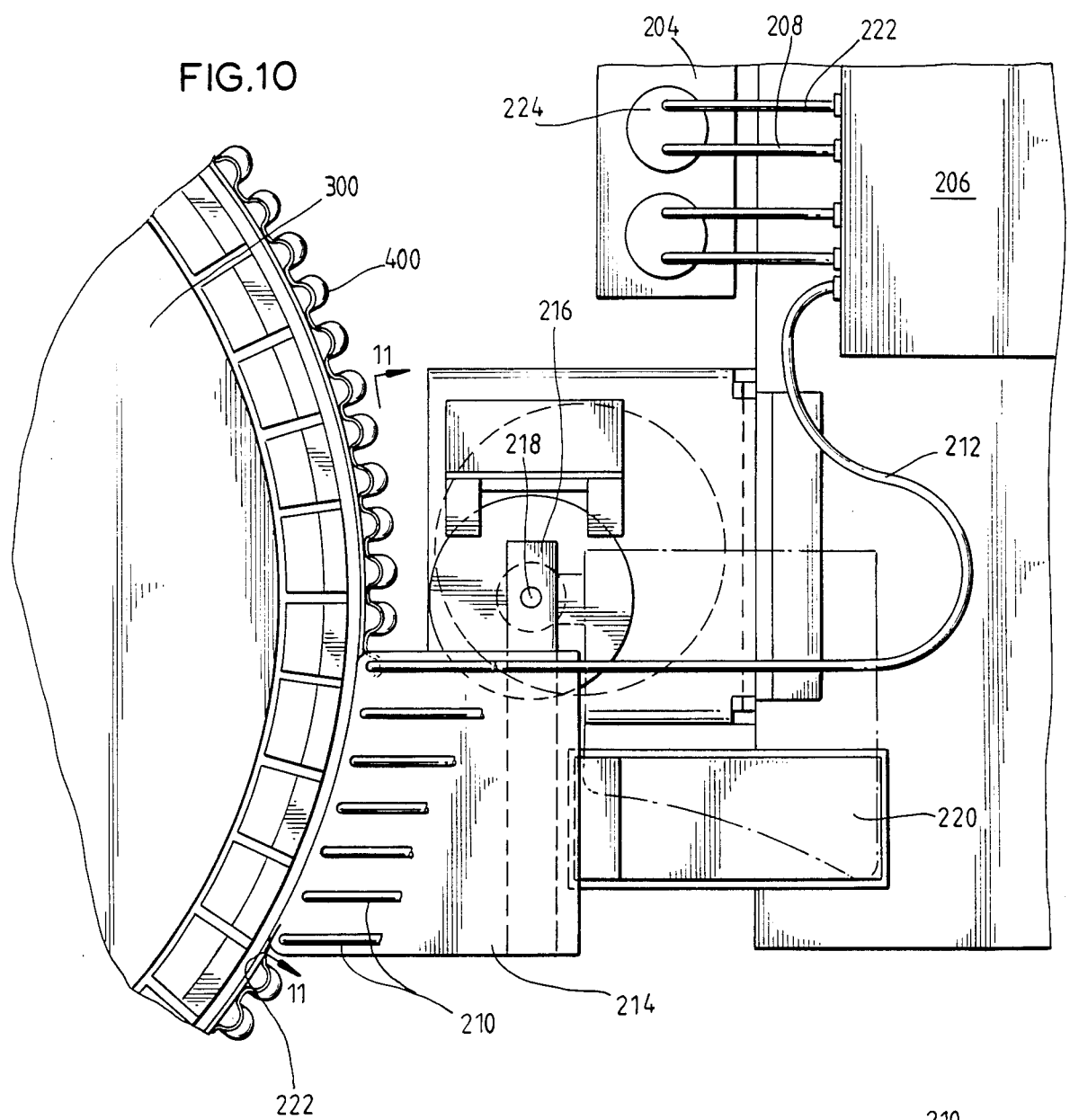
FIG. 10 is an enlarged partial plan view taken generally along the section line 10—10 of FIG. 2.
Figure 11:
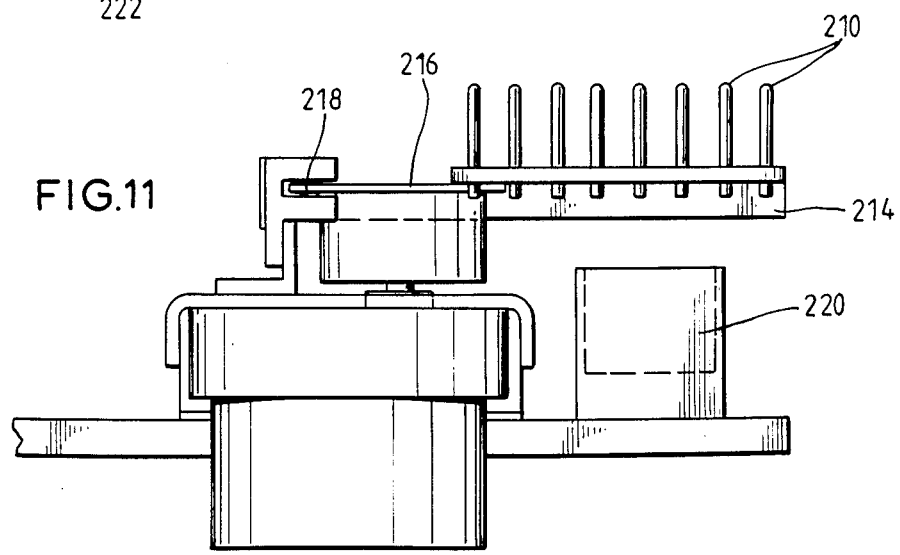
FIG. 11 is a section view taken generally along the curved arc 11—11 in FIG. 9.

The reagent dispensing device 200, shown in FIGS. 2, 10, and 11 includes the stoppers 224 engaged with the reservoir cover 204 and the reservoirs 202. The air tubes 222 and the exit tubes 208 protrude from the stoppers 224 and go into the reagent pump 206. The reagent is pumped out of the reservoirs 202 into the reagent pump 206 and thereafter through the tubes 212 to the outlets 210. The outlets 210 are mounted on the outlet support 214. The outlets 210 discharge reagent simultaneously into the appropriate number of cuvettes 402 aligned directly under the outlets 210. The arcuate edge 222 of the outlet support 214 has the same radius of curvature as the centrifuge rotor 300 and extends beneath the cover 16. The outlet support 214 can be pivoted at the pivot point 218 by the arm 216. When pivoted at point 218, the outlets 210 are located above the flush reservoir 220. The reagent dispensing device 200 is cleaned by flushing solution through the device 200 into the flush reservoir 220.

Figure 16:
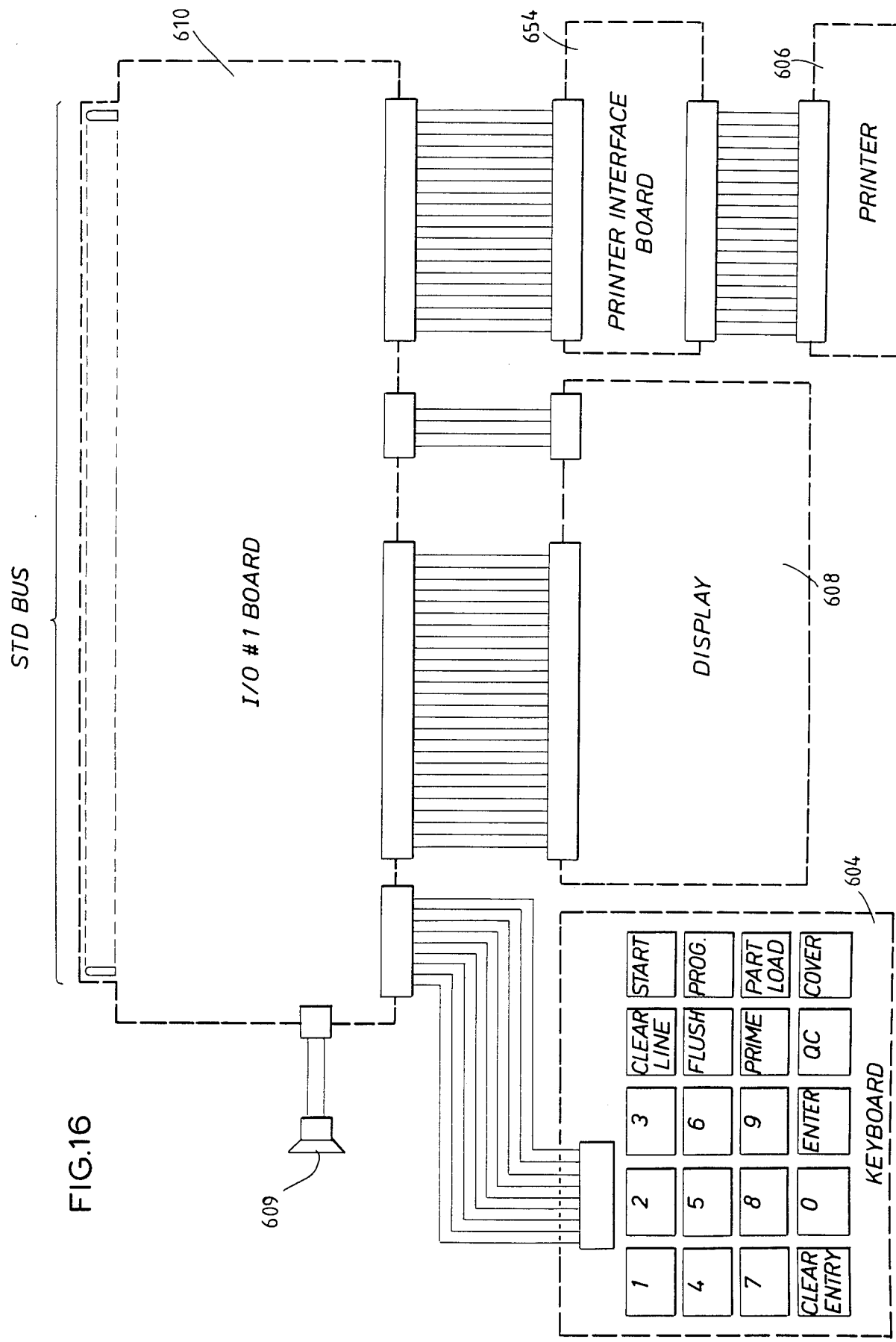
FIG. 16 is a schematic diagram of one embodiment of a first Input/Output Board and the associated peripherals as practiced in one embodiment of the present invention.

The microprocessor or central processing unit (CPU) 600 controls the first I/O board 610, the second I/O board 612 and the third I/O board 646, as shown in FIG. 15. The first I/O board 610, shown in FIG. 16, connected to the CPU 600 by the STD bus, controls the input from and the output to the keyboard 604, the display 608, the buzzer 609 and the printer 606. In the present invention, a printer interface board 654 is used to transfer data between the first I/O board 610 and the printer 606.

Figure 17:
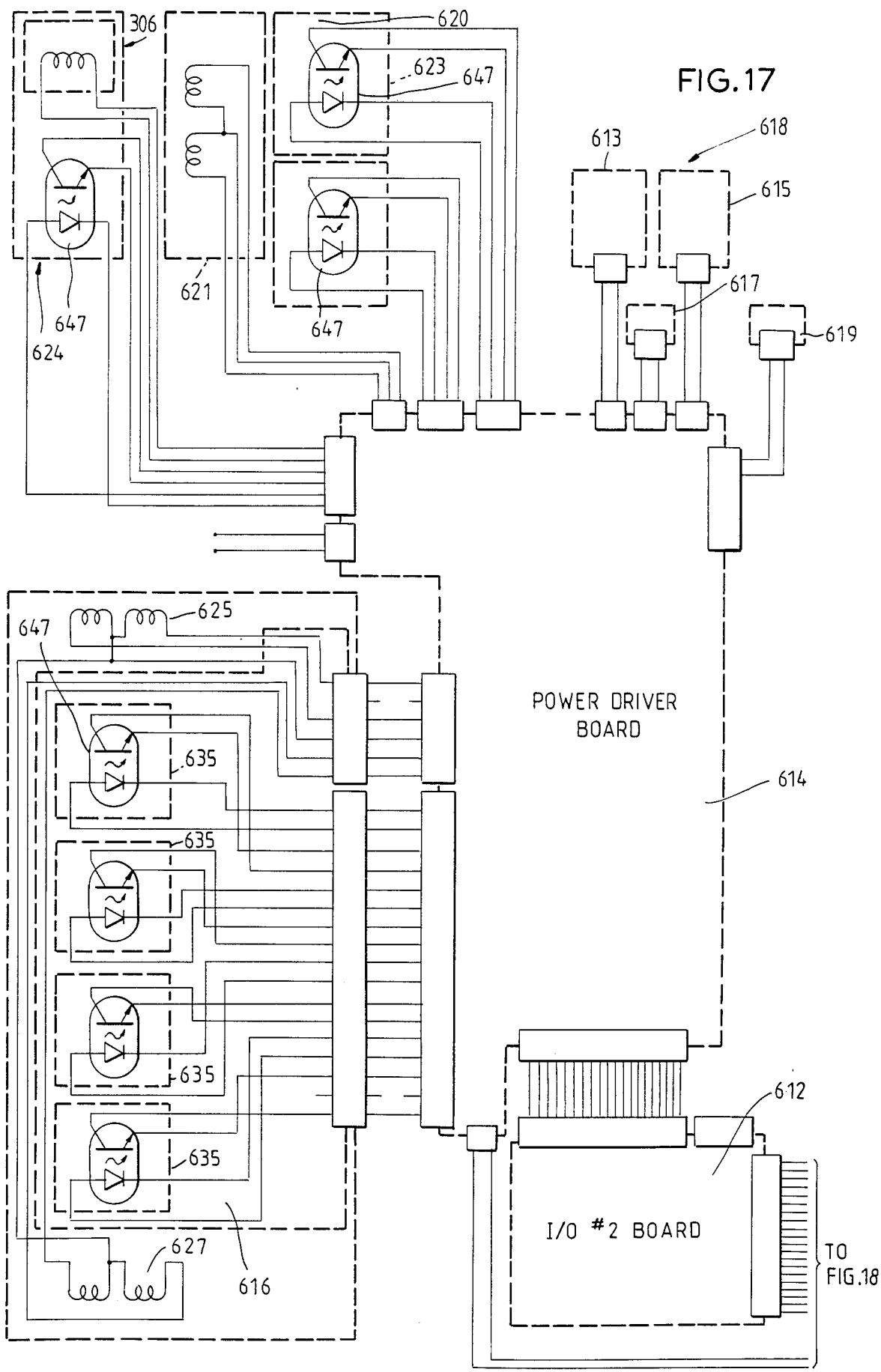
FIG. 17 is a partial schematic diagram, continued in FIG. 18, of one embodiment of the power driver circuitry and the associated peripherals as practiced in one embodiment of the present invention.

The second I/O board 612 controls the power-driver board 614 and the motor-driver board 628, as shown in FIG. 17. The power-driver board 614 controls the pump assembly 618, including the air pump 615, peristaltic pump 615, air valves 617, and air pressure sensor 619. The board 614 also controls the gear motor component 620, including the gear motor 621 and gear motor sensor 623, the solenoid 306, the cover 16 interlock sensor 624 and the reagent valve assembly 616, including the valve motors 625, 627. The cover interlock sensor 624 insures that the cover 16 is closed and provides an appropriate indication on the keyboard 604 (FIG. 16) if the cover 16 is open. The air pump 613 supplies air through the air valves 617 and pressure sensors 619 to the air tubes 222 and the peristaltic pump 615 to control the dispensing of fluid from the dispensing device 200. The reagent valve assembly 618 includes two rotary multipart valves driven by the valve motors 625, 627. The valve position sensors 635 enable selective dispensing from the reservoirs 202. The gear motor 621 is operative to index the carousel from one angular position to the next through the engagement of the stanchion 118 by the axle 119.

Figure 18:
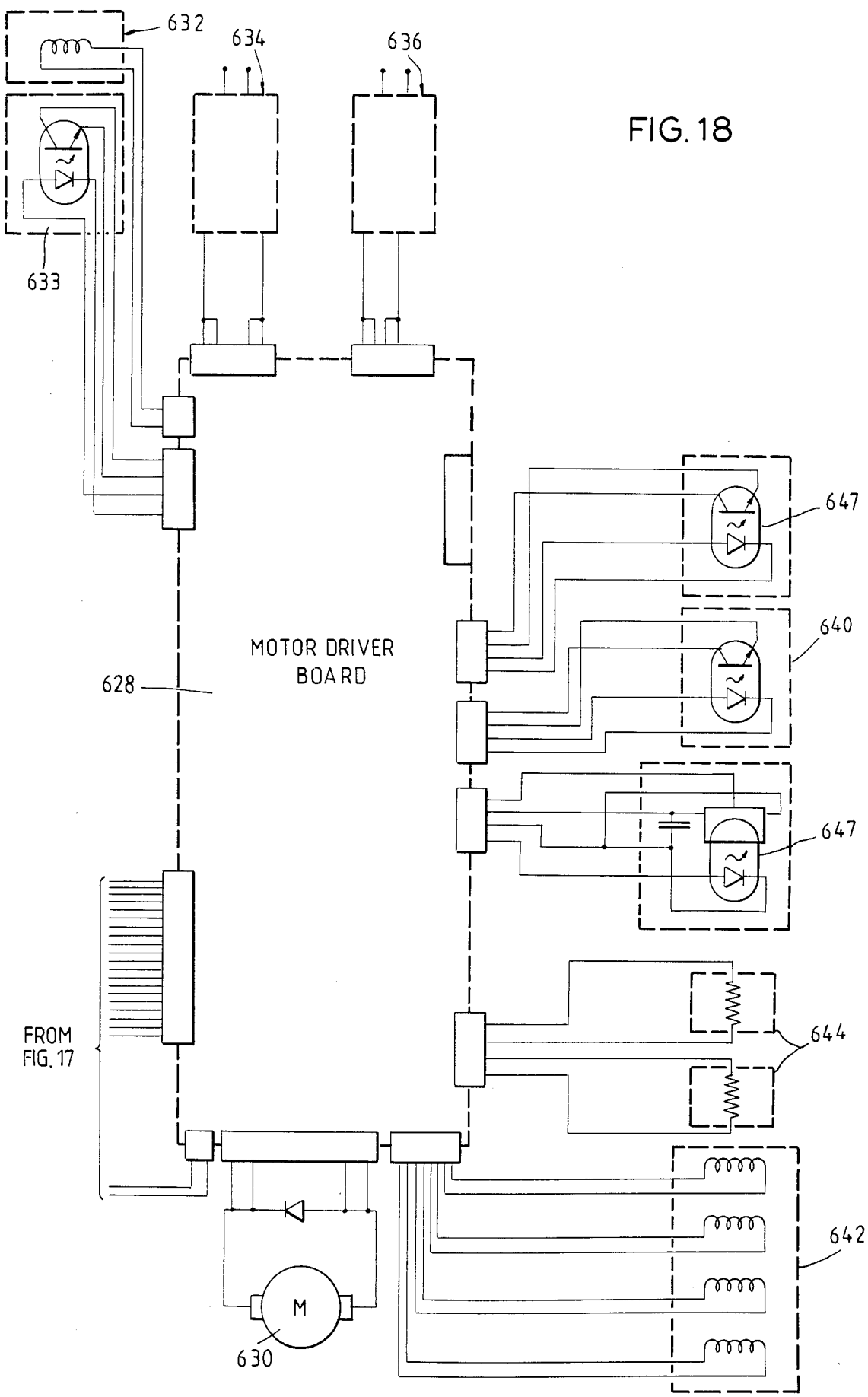
FIG. 18 is a partial schematic diagram, continued from FIG. 17, of one embodiment of the second motor driver circuitry and the associated peripherals as practiced in the present invention.

As shown in FIG. 18, the motor-driver board 628 powers the clutch control 632, clutch sensor 633 the power supply 634 for the stepping motor 308, the power supply 636 for the variable speed motor 304, the light source 502, the controls 640 for the linear optical detector 522, the heat sink 644, and the controls 642 for the stepping motor 308, and the servo motor 630, as shown in FIG. 18. The servo motor 630 controls the positioning of the arm 108. The clutch sensor 633 may be an optical sensor which detects the present clutch 330 position. The third I/O board 646, shown in FIG. 15, controls the video display 603. Isolators 647 are used for optically isolating the various controls and motors from the digital microcomputer components.

Figure 19:
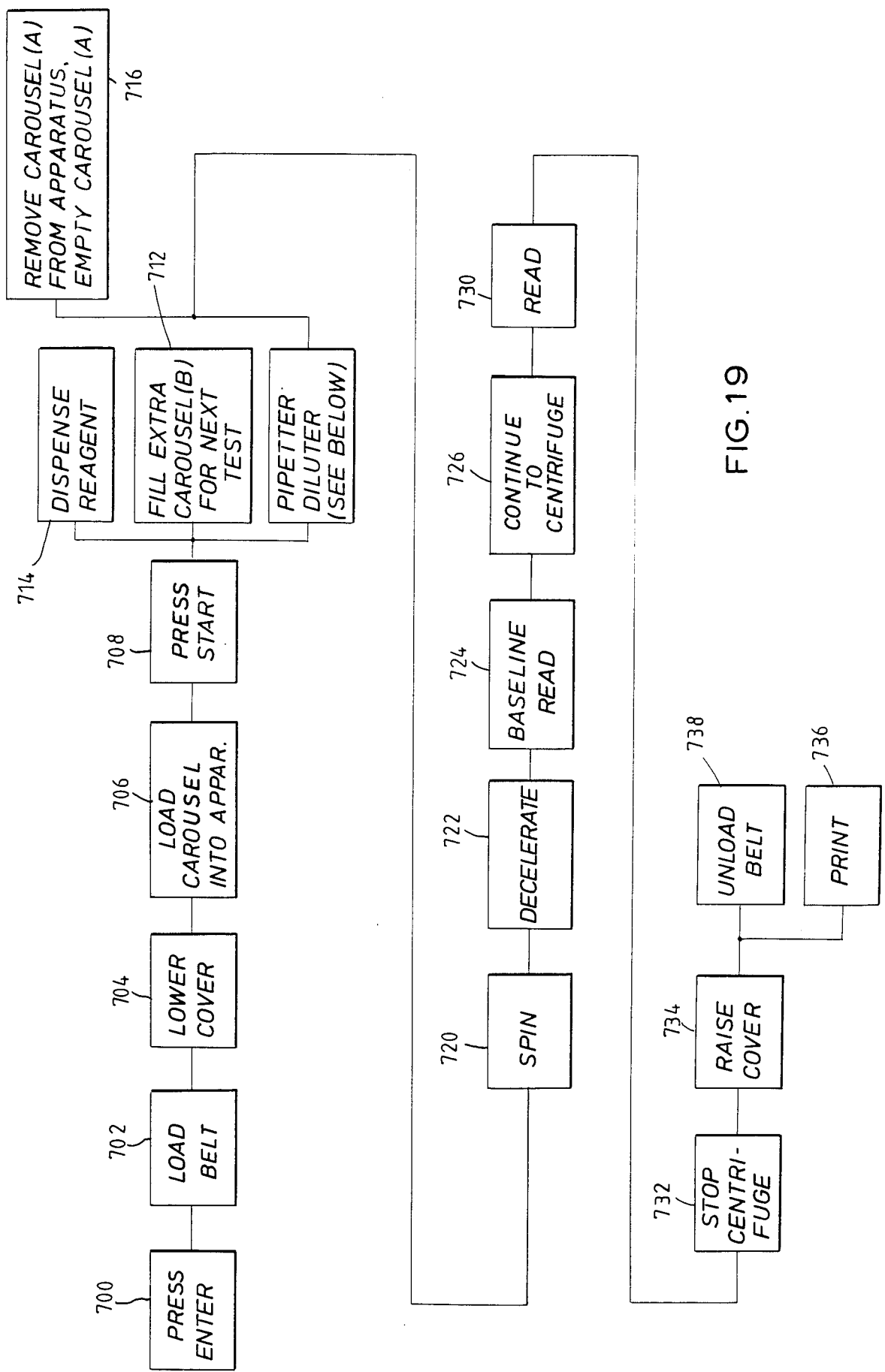
FIG. 19 is a flow chart of one embodiment of the present invention.

The method of the present invention is schematically described in FIG. 19 and is efficiently practiced utilizing the apparatus of the present invention. The analysis sequence is initiated by pressing the "enter" button on the keyboard 604 (step 700). The disposable belt 400 is manually loaded onto the centrifuge rotor 300 and secured by the belt supports 302 (step 702). The cover 16 is lowered to enclose the centrifuge rotor 300 and the disposable belt 400 (step 704). A blood specimen of approximately 1.0 milliliter is acquired from each patient and manually placed in the insert 136 of a specimen tube 134. However, a 6–7 milliliter sample may be routinely used with test tube 134 without the insert 136. Each specimen tube 134 has a coded bar label 144 attached thereto. The specimen tubes 134 are centrifuged to separate the blood specimens into red blood cells and supernatant. The specimen tubes 134 having the separated blood specimen (red cells and plasma) are manually placed into the peripheral apertures 124 in the carousel 114. The dilution cups 134a are normally placed in the interior apertures 122 in the carousel 114. The carousel 114 is loaded into the trough 128 of the apparatus 10 (step 706).

The analysis is begun by pressing the "start" button on the keyboard 604 (step 708). The reagent dispensing device 200 simultaneously dispenses the correct reagents into seven cuvettes 402 of the disposable belt 400 (step 714). The pipetter-diluter device 100 is activated (step 710) to prepare the specimen for analysis (step 710). The operation of the pipetter-diluter device 100 (step 710) will be described in more detail later. During the time the pipetter-diluter device 100 and the reagent dispensing device 200 are operating, an extra carousel 114 can be prepared for the next test (step 712).

The reagents are held in the reagent reservoirs 202. Reagents typically used include antisera, anti-A, anti-B, anti-A-B and anti-D, A1 reagent red cells, A2 reagent red cells, B reagent red cells, O reagent red cells and control. In addition, Rh pheno typing antiserums such as anti C, c, E and e may be used. Other direct agglutinating antiserums such as anti-M, anti-N, anti-P and anti-K can also be used.

After the reagent dispensing device 200 has dispensed the correct amount of reagent into the cuvettes 402 and the pipetter-diluter device 100 has prepared and transferred the specimen to the cuvettes 402, the carousel 114 can be removed from the apparatus 10 and emptied (step 716). The centrifuge rotor 300 is then accelerated to a velocity sufficient to compact the sample into the extreme radial apex 412 of the cuvette 402 (step 720). The centrifuge rotor 300 is decelerated to a velocity where the gravitational attraction is slightly greater than the centrifugal force on the specimen so that streaming of the opaque particles is possible in negative particles (step 722). A baseline reading of the optical characteristics of the sample in each cuvette 402 is automatically taken using the optical system 500 (step 724) before any significant streaming can occur. The optical system 500 determines the vertical dimension (VI in FIG. 9B) of the opaque portion of the sample. The baseline reading is critical for determining an accurate indication of a possible reaction. The rotating speed must be slow enough for the optical system 500 to make the necessary measurements, while the rotor 300 is spinning, on a continuous basis in a strobing fashion. Thus the speed of rotation is limited by the capability of the optical technology utilized.

Figure 9A:
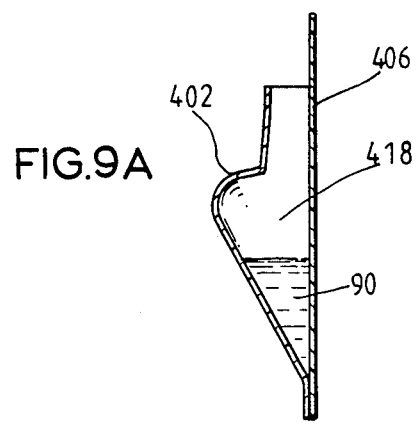
FIGS. 9 are vertical cross-sectional views taken generally along the line 9—9 in FIG. 6 at different stages during the use of the present invention illustrating the positions of the sample, compacted red blood cells, supernatant and streaming red blood cells.
Figure 9B:
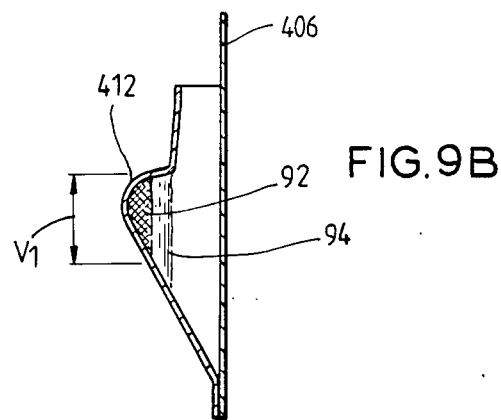
Figure 9C:
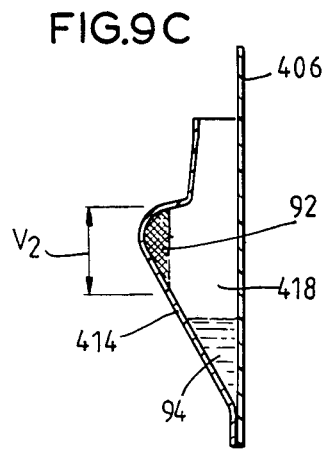
Figure 9D:
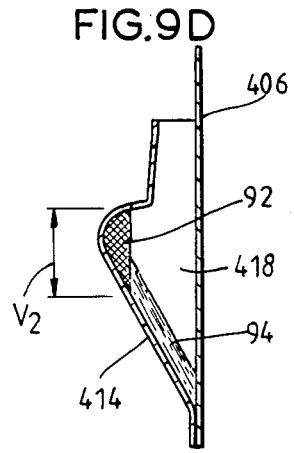
Figure 9E:
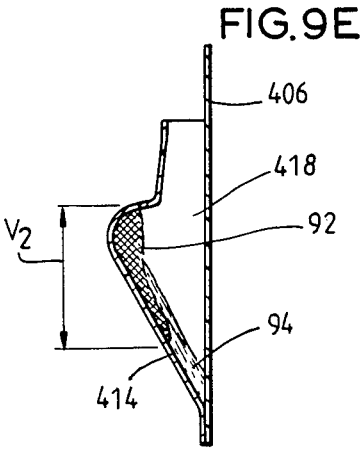

After sufficient time has elapsed (e.g., 25 secs.) for streaming in a negative test to be completed, the optical system 500 automatically reads the reaction which occurred (step 730), i.e., the vertical dimension in FIG. 9C–9E, of the opaque portion of the sample is determined. After the final reading has been taken, the centrifuge rotor 300 stops (step 732), the cover 16 can be raised (step 734), the printer 606 and the display 608 are activated (step 736) and the single use belt 400 can be manually unloaded. All of the data taken has been stored in the microprocessor 600 for analysis.

The baseline reading (step 724) can be automatically compared by the CPU 600 with the final reading (step 730) to determine any abnormality or malfunction associated with the specific sample. For example, the baseline reading may indicate that the sample had "slipped out" of the radial apex 412 of the cuvette 402. Such slippage could be interpreted as the streaming of the sample caused by agglutination rather than by the fact that the entire opaque portion of the sample slid down in position which would be an incorrect reading. The procedure for determining the baseline characteristics of the sample prevents misreading in this and similar situations.

When a "slipped" reaction 84, shown in FIG. 6, is noted, the microprocessor 600 requires the printer 606 or the display 608 to note the inconsistency of the reading with a "?". A weak reaction mass 88, shown in FIG. 6, is illustrated adjacent the negative reaction mass 86. A weak reaction could be related to specific biological parameters by the microprocessor 600 and indicated by the display 608 or the printer 606.

The second vertical measurement V2, as illustrated in FIGS. 9C, 9D and 9E, is compared by the microprocessor 600 with the first vertical measurement V1, as illustrated in FIG. 9B, by subtracting V2 from V1. If the difference between V1 and V2 exceeds a preset difference as determined by the microprocessor 600, a negative reaction is indicated. If the difference does not exceed the preset value as determined by the microprocessor 600, a positive reaction is indicated, as shown at 82 in FIG. 6. No agglutination (i.e. streaming) indicates a negative test and agglutination (no streaming) indicates a positive test.

It will be understood that by taking the vertical measurements V1 and V2 of the compacted red blood cells of each individual sample, the present invention provides baselining for each sample. The utilization of baselining in the present invention provides a standard against which measurements can be compared. Further, such baselining as illustrated in FIGS. 9A through 9E, eliminates any effects on the determination of reactions due to variations in the volume or concentration of the opaque particles of the specimen. Still further, and perhaps more significantly, such baselining eliminates any effect in differentiating between positive and negative reactions due to extraneous vertical downward movement of the compacted red blood cells, as indicated at 84 in FIG. 6. Such downward movement is known to occur and without baselining would indicate a false negative reaction.

The microprocessor 600 evaluates the reaction by reading the responses of the individual photosensitive elements (pixels) of the linear optical detector 522 in sequence based upon the absorbed energy. The image of the compacted red blood cells shadows the individual photosensitive elements (pixels). The pixels shadowed by the projection of the compacted red blood cells onto the linear optical detector 522 have low energy output. The pixels exposed directly to the light rays 509 and not shadowed by the compacted red blood cells 92 have a high energy output. The number of the low output, dark pixels 530 is directly proportional to the length of the compacted red blood cells 92 in the cuvette 402. If there are significantly more low output, dark pixels due to the streaming red blood cells, this would indicate a negative reaction. The strength or weakness of the reaction would be proportional to the increase in the number of low output, dark pixels on the linear optical detector 522. The magnitude of the dimension of the image or shadow produced can be used as a comparison to determine the presence and magnitude of a reaction between a red blood cell specimen and a reagent. A battery of such measurements is determinative of blood type.

Figure 20:
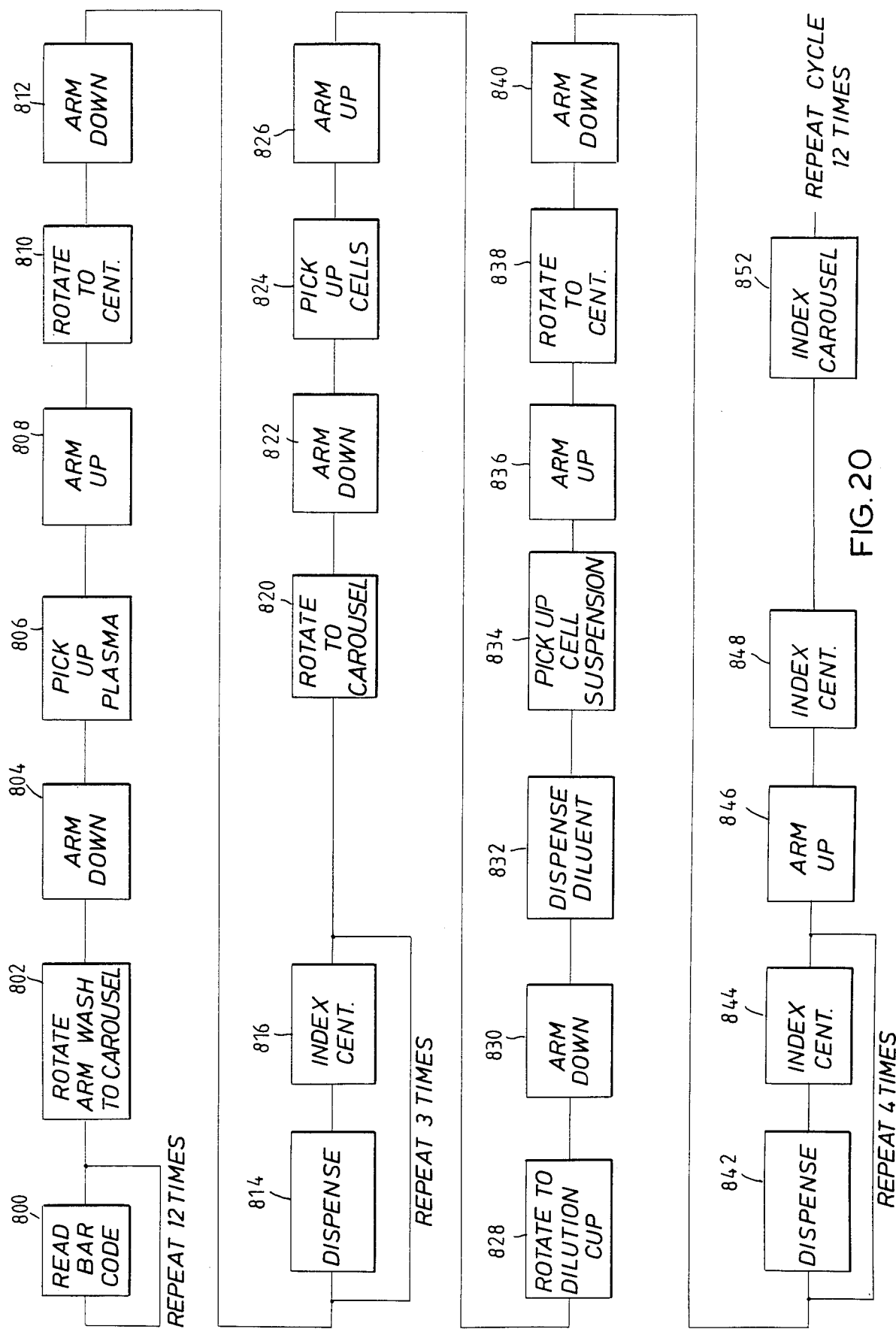
FIG. 20 is a flow chart of one embodiment for preparing the samples for practicing the present invention The above general description and the following detailed description are merely illustrative of the generic invention, and additional modes, advantages and particulars of this invention will be readily suggested to those skilled in the art without departing from the spirit and scope of the invention.

FIG. 20 illustrates the automated sequence performed by the pipetter-diluter 100. Initially, the bar coded labels 144 on twelve tubes 134 in the carousel 114 are read by a conventional optical code reader 24 (step 800). The arm 108 is rotated to be aligned over the first tube 134 in the carousel 114 (step 802). The arm 108 is lowered to allow the needle 106 to engage the less dense supernatant (plasma) that rests above the red blood cells in the tube 134 (step 804). The needle 106 withdraws about 90 microliters of the supernatant (step 806). The arm 108 is raised to disengage the carousel 114 (step 808). The arm 108 is rotated to be aligned with the aperture 18 in the cover 16 over the centrifuge rotor 300 (step 810). The arm 108 is lowered to position itself just above a first cuvette 402 in the disposable belt 400 (step 812). The pipetter-diluter device 100 dispenses about 30 microliters of the supernatant into the cuvette 402 (step 814). The centrifuge rotor 300 is automatically indexed by the microprocessor 600 to locate another cuvette 402 directly beneath the needle 106 (step 816). The pipetter-diluter device 100 repeats the process of dispensing about 30 microliters of the supernatant into three cuvettes 402.

After the three cuvettes 402 that already contained the required reagents (See FIG. 19, step 714) have received about 30 microliters each of supernatant, the arm 108 is lifted to disengage from the cover 16. The arm 108 is rotated to again align the needle 106 with the first tube 134 in the carousel 114 (step 820). The arm 108 is lowered into the tube 134 through the supernatant to engage the red blood cells in the lower extremity of the tube 134 (step 822). The pipetter-diluter device 100 extracts about 20 microliters of the red blood cells from the lower extremity of the tube 134 with the needle 106 (step 824). The arm 108 is lifted to disengage the carousel 114 (step 826). The arm 108 is rotated to align the needle 106 with a corresponding dilution cup 134a. The dilution cup 134a is used to dilute the red blood cells extracted from the outer tube 134 (step 828). The arm 108 is lowered into the dilution cup 134a (step 830).

The pipetter-diluter device 100 utilizing the syringe 102 and the needle 106 dispenses the red blood cells and a diluent into the dilution cup 134a (step 832). The dispersion of the red blood cells and the diluent into the inner cup 134a is sufficient to cause adequate mixing of the red blood cells and the diluent. Typically, for human blood, the pipetter-diluter device 100 mixes about 465 microliters of the diluent with about 20 microliters of the red blood cells to form a cell suspension having approximately a 3.5% concentration. The 3.5% cell suspension provides optimal reading characteristics for the presently preferred embodiment of the present invention.

The needle 106 extracts about 120 microliters of the 3.5% cell suspension from the inner cup 134a (step 834). The arm 108 lifts to disengage from the carousel 114 (step 836). The arm 108 rotates to again be aligned with the aperture 18 in the cover 16 (step 838). The needle 106 is lowered into the aperture 18 to be aligned above the fourth cuvette 402 which already contains an appropriate reagent (step 840). The pipetter-diluter device 100 dispenses approximately 30 microliters of the 3.5% cell suspension into the cuvette 402 with the needle 106 (step 842). The centrifuge rotor 300 automatically indexes to the next appropriate cuvette (step 844). The dispense-index sequence is continued until a total of four cuvettes containing an appropriate reagent have accepted the 30 microliters of the 3.5% cell suspension. Thereafter, the arm 108 is lifted to disengage from the cover 16 (step 846). The centrifuge rotor 300 is indexed to the next appropriate cuvette 402 (step 848). The carousel 114 is indexed to align the next tube 134 (step 852) with the path of the needle 106 and the cycle begins again (step 802) and is repeated for all twelve specimens in each tube 134.

The needle 106 is washed between patients in the wash station 116 by purging with a cell suspending solution contained in the diluent reservoir 104. The red cell suspending solution may comprise anhydrous dextrose, sodium chloride, sodium citrate, citric acid, deionized water, chloramphenicol, neomycin sulfate, and imosine.

When the fluid assay system 10 is not in use overnight the reagent reservoirs 202 may be removed and replaced with bottles containing sterile water. The reagent dispensing device 200 flushes the lines with the water to leave the water in the reagent dispensing device 200 when the device is not being used. Similarly, the reagent dispensing device 200 can be flushed with a bleach solution and water at periodic intervals to clean the interior components of the reagent dispensing device 200.

The number of cuvettes 402 to receive supernatant, the number of reagents utlized, and the number of specimens handled by the system 10 may be preprogrammed by an operator. Further, the volume of specimen withdrawn from the carousel may be varied.

The method of the present invention can be utilized with any specimen that can be separated by density and contains opaque material that has physical reactions with a specific reagent. It is preferable that the reactions cause the opaque portion of the specimen to become more fluid or less fluid depending upon the characteristics of the specimen.

Additional advantages and modifications of the present invention will readily occur to those skilled in the art. The invention in its broader aspects is therefore not limited to the specific details, representative apparatus, and the illustrative examples shown and described herein. Accordingly, departures may be made from the detail without departing from the spirit or scope of the disclosed general inventive concept.

What is claimed is:

1. An apparatus for determining the reactive characteristics of a biological mixture of a specimen and a reagent comprising:
   (a) a centrifuge rotor;

(b) an energy transmissive, flexible belt formable into a cylinder and removably mounted for movement in unison with said centrifuge rotor, said belt including a plurality of specimen containers, said specimen containers each including a flat element having an inner surface, an outer surface, an upper surface and a lower end, and an indented element having an inner surface, an outer surface, an upper end and a lower end, and having at least one smooth, outwardly, radially extending and vertically oriented indentation formed therein, the indentation vertically gradually increasing in an outwardly extending radial depth along a moderatley inclined slanting segment to a smoothly curved radial apex then abruptly decreasing in radial depth along a severely inclined segment and thereafter extending upwardly along a uniformly shallow generally vertical segment to the upper end of said indented element, said flat element and said indented element being connected together with the inner surface of the flat element in contact with the inner surface of said indented element, said open upper end of said indented element forming an opening for filling said specimen containers; and (c) a detection system for irradiating the plurality of specimens contained within said belt and for optically measuring the reactive characteristics of the specimens.

2. An apparatus as described in claim 1 including means for automatically making a first reading of a linear dimension of specimens contained in said belt, means for automatically making a second reading, after the lapse of a period of time, of a linear dimension of specimens contained in said belt and means for automatically comparing said first and second readings.

3. An apparatus as described in claim 1 wherein said centrifuge rotor comprises:
(a) an essentially horizontal circular planar member;
(b) a cylindrical member having an upper end, a lower end, an inner surface and an outer surface; and
(c) an annular member fixedly securing said planar member perpendicular to the central axis of said cylindrical member said annular member disposed at an acute angle with the plane of the planar member and the central axis of said cylindrical member, a plurality of recesses formed in said annular member and said upper end of said cylindrical member said recesses adapted to align with said indentations in said indented element.

4. An apparatus as described in claim 3 further comprising a plurality of supports fixedly secured to the lower end of said cylindrical member and extending upwardly for removably securing said energy transmissive belt to said centrifuge rotor.

5. An apparatus as described in claim 1 including a housing adapted to contain said centrifuge rotor and said detection system, said apparatus further including a pipetter-diluter device mounted in said housing, said pipetter-diluter device comprising:
(a) a syringe for withdrawing fluid from a reservoir, holding fluid and discharging fluid,
(b) a conduit needle operationally associated with said syringe for insertion into the fluid to permit said syringe to withdraw or discharge the fluid,
(c) a carousel, and
(d) a plurality of reservoirs interposed in said carousel from which said conduit needle and said syringe can withdraw fluid or into which said conduit needle and said syringe can discharge fluid.

6. An apparatus as described in claim 5 wherein said carousel comprises:
(a) a stanchion, and
(b) a plurality of flat circular plates fixedly engaged with and perpendicular to said stanchion for accepting and for securing said plurality of reservoirs, said plurality of flat circular plates comprising a top plate having apertures conforming to the associated cross-sections of and securing the relative position of said reservoirs, a bottom plate for supporting said reservoirs, and an intermediate plate having apertures conforming to the associated cross-sections of and securing the relative position of said reservoirs.

7. An apparatus as described in claim 1 wherein said carousel includes a plurality of receptacles, said receptacles having coded bar labels on said receptacles, said apparatus further including a coded bar label reader arranged to read the labels on said receptacles, said apparatus including means for indexing said carousel past said reader.

8. An apparatus as described in claim 7 including means for automatically inserting reagents and specimens into said plurality of containers in the proper amounts.

9. An apparatus for determining the reactive characteristics of a biological mixture of a specimen and a reagent comprising:
a centrifuge including receptacles for a plurality of separate specimen and reagent containing samples;
a device for automatically measuring at least one dimension of each of said samples in said receptacles while said centrifuge is rotating; and
a comparator for comparing, for each sample, a representation of a first measurement of a dimension made by said device with a representation of a subsequent measurement of a corresponding dimension made by said device.

10. An apparatus as described in claim 9 wherein said centrifuge includes a removable flexible belt having said receptacles formed in said belt.

11. An apparatus as described in claim 9 wherein said device automatically makes a subsequent measurement of a vertical dimension of each of said samples after the expiration of a predetermined time period following the first measurement.

12. An apparatus as described in claim 9 werein said comparator is adapted to compare the difference between said first and subsequent measurements with a predetermined difference indicative of a reactive characteristic between said specimen and reagent.

13. A specimen holder for a centrifuge apparatus adapted to determine the reactive characteristics of a biological mixture of a specimen and a reagent, said holder comprising an energy trnasmissive, flexible, disposable belt having a pair of opposed sides and side edges, said belt being formable into a cylinder and removably mountable for movement in unison with a centrifuge apparatus, said belt having a plurality of specimen containers formed integrally in said belt and spaced at regular intervals along the length of said belt, said containers extending outwardly from one of said sides of said belt, and the other of said sides of said belt being flat, each of said containers having a filling opening near the same side edge of said belt and each of said containers having a first face generally conincident with the plane of said belt and an opposite face, said opposite face including a smoothly curved radial apex spaced outwardly from the plane of said belt and a portion which is inclined with respect to said plane of said belt and which connects said apex to the remainder of said belt, said portion vertically gradually increasing in an outwardly extending radial depth along a moderately inclined slanting segment to said apex then abruptly decreasing in radial depth along a severely inclined segment and thereafter extending upwardly along a uniformly shallow generally vertical segment ot said filling opening.

14. The specimen holder of claim 13 wherein said holder is optically transparent.

15. The specimen holder of claim 14 wherein each of said sides is formed of a sheet of plastic film, said sides being connected to one another.

* * * * *